US010537135B2

(12) United States Patent
Smith et al.

(10) Patent No.: US 10,537,135 B2
(45) Date of Patent: Jan. 21, 2020

(54) SYSTEM AND METHOD OF OBTAINING SMOKING TOPOGRAPHY DATA

(71) Applicant: Altria Client Services LLC, Richmond, VA (US)

(72) Inventors: Barry S. Smith, Hopewell, VA (US); Douglas A. Burton, Glen Allen, VA (US)

(73) Assignee: Altria Client Services LLC, Richmond, VA (US)

( * ) Notice: Subject to any disclaimer, the term of this patent is extended or adjusted under 35 U.S.C. 154(b) by 1012 days.

(21) Appl. No.: 14/205,717

(22) Filed: Mar. 12, 2014

(65) Prior Publication Data

US 2014/0278250 A1 Sep. 18, 2014

Related U.S. Application Data

(60) Provisional application No. 61/800,226, filed on Mar. 15, 2013.

(51) Int. Cl.
*A24F 47/00* (2006.01)
*G01N 19/00* (2006.01)
*G01N 27/00* (2006.01)

(52) U.S. Cl.
CPC ........... *A24F 47/002* (2013.01); *G01N 19/00* (2013.01); *G01N 27/00* (2013.01)

(58) Field of Classification Search
CPC ... A61M 11/005; A24F 47/008; A24F 47/002; F23N 5/242; B60N 3/14; A24C 5/3406;

(Continued)

(56) References Cited

U.S. PATENT DOCUMENTS 4,771,381 A * 9/1988 Norman ............... A24C 5/3406
131/330
4,787,410 A * 11/1988 Fujieda ................. F23N 5/242
137/554

(Continued)

FOREIGN PATENT DOCUMENTS

CN 202233002 U 5/2012
CN 102970885 A 3/2013

(Continued)

OTHER PUBLICATIONS

Office Action for corresponding Kazakhstan Application No. 2015/1182.1 dated Mar. 17, 2017 and English translation thereof.

(Continued)

*Primary Examiner* — Regis J Betsch
*Assistant Examiner* — Kaleria Knox
(74) *Attorney, Agent, or Firm* — Harness, Dickey & Pierce, P.L.C.

(57) ABSTRACT

An exemplary smoking topography circuit of an electronic aerosol smoking article, includes at least one sensor configured to measure user interaction with the smoking article, a processor, and memory. The processor is configured to detect a smoking event based an output of the at least one sensor, collect data associated with the smoking event, and arrange the data in a pattern that associates the smoking event to shifts in battery voltage. The memory is configured to store the data pattern in a structured multi-byte format.

30 Claims, 6 Drawing Sheets

(58) Field of Classification Search
CPC ...... A61B 5/0404; G01N 19/00; G01N 27/00; B60L 3/12
USPC ............. 128/202.21; 131/329, 330; 320/104; 200/5 A; 137/554; 600/523
See application file for complete search history.

(56) References Cited

U.S. PATENT DOCUMENTS

| | | | |
|---|---|---|---|
| 5,060,671 A * | 10/1991 | Counts | A24F 47/008 128/202.21 |
| 5,372,148 A | 12/1994 | McCafferty et al. | |
| 5,454,870 A | 10/1995 | Sieberth | |
| 5,514,630 A | 5/1996 | Willkens et al. | |
| 5,613,505 A | 3/1997 | Campbell et al. | |
| 6,040,560 A * | 3/2000 | Fleischhauer | A24F 47/008 128/202.21 |
| 6,814,083 B2 | 11/2004 | Likness et al. | |
| 7,358,701 B2 * | 4/2008 | Field | B60L 3/12 320/104 |
| 2003/0226837 A1* | 12/2003 | Blake | A24F 47/008 219/260 |
| 2004/0031497 A1 | 2/2004 | Likness et al. | |
| 2011/0036346 A1 | 2/2011 | Cohen et al. | |
| 2011/0265806 A1 | 11/2011 | Alarcon et al. | |
| 2012/0048266 A1* | 3/2012 | Alelov | A61M 11/005 128/202.21 |
| 2012/0089039 A1* | 4/2012 | Felix | A61B 5/0404 600/523 |
| 2012/0291791 A1 | 11/2012 | Pradeep | |
| 2013/0192615 A1 | 8/2013 | Tucker et al. | |
| 2013/0319440 A1* | 12/2013 | Capuano | A24F 47/008 131/329 |
| 2013/0340750 A1* | 12/2013 | Thorens | A24F 47/008 128/202.21 |
| 2014/0116455 A1* | 5/2014 | Youn | A24F 47/008 131/329 |
| 2014/0123990 A1* | 5/2014 | Timmermans | A24F 47/008 131/328 |

FOREIGN PATENT DOCUMENTS

| | | | | |
|---|---|---|---|---|
| EP | 0857431 A1 | 8/1998 | | |
| WO | WO94/02256 | * | 2/1994 | ............. A24F 47/00 |
| WO | WO94/18860 | * | 9/1994 | ............. A24F 47/00 |
| WO | WO 94/18860 A1 | 9/1994 | | |
| WO | 2008154441 A1 | 12/2008 | | |
| WO | WO-2012/109371 A2 | 8/2012 | | |
| WO | WO 2012/120487 A2 | 9/2012 | | |

OTHER PUBLICATIONS

Office Action for corresponding Chinese Application No. 20148001617.4 dated Jun. 12, 2017 and English translation thereof.
Office Action for corresponding Russian Application No. 2015144314 dated Jul. 31, 2017 and English translation thereof.
International Search Report and Written Opinion for PCT/US2014/024612 dated Oct. 1, 2014.
Office Action for corresponding Kazakhstan Application No. 2015/1182.1 dated Dec. 14, 2016 English translation thereof.
Examination Report dated Jun. 27, 2019 in Indian Patent Application No. 5574/CHENP/2015.
Communication pursuant to Article 94(3) EPC dated Jun. 19, 2018 in European Patent Application No. 14 714 897.7.

* cited by examiner

SYSTEM AND METHOD OF OBTAINING SMOKING TOPOGRAPHY DATA

RELATED APPLICATION

This application claims priority under 35 U.S.C. § 119(e) to U.S. Application No. 61/800,226 filed on Mar. 15, 2013, the content of which is hereby incorporated by reference in its entirety.

FIELD

This disclosure relates to an electronic aerosol smoking article, and particularly to a system and method of obtaining smoking topography data from an electronic smoking article.

WORKING ENVIRONMENT

Smoking articles including electronic cigarettes or e-cigarettes use a liquid as the aerosol-forming substrate reduce secondhand smoke, while permitting a smoker to selectively suspend and reinitiate smoking. These devices can include a cartridge that contains the aerosol forming substrate. The substrate can come in various forms such as a solid or liquid and releases an aerosol gas to the smoker following the appropriate application of heat through a heating element. The heating element is powered through a power supply, such as a battery. The heating of the aerosol substrate is triggered via e-puff sequence initiated by the user.

Various systems have been described which collect data based on the smoking topography of the individual. For example, US 2012/0291791 discloses a nicotine delivery reduction system having a breath monitor that tracks nicotine solution usage, usage frequency, and breath characteristics. A flow controller is used to regulate the levels of nicotine or nicotine solution provided to a user based on monitored user habits and characteristics. US 2011/0036346 discloses a personal inhalation device that includes a logic circuit that can be programmed to limit an amount of nicotine media atomized during a puff, and the minimum time interval between activations of the atomizing device, for example. The logic circuit can be programmed to retain device operation information such as puffs per day, puffs per minute, cartridges used, average use, and other usage information as desired. The collected data is stored in memory and can be later downloaded to an external device.

US 2011/0265806 is directed to an electronic smoking article that includes a controller that carries out various operations on the device and a memory that stores instructions to be executed by the controller and may store usage information, product information, and user information. For example, the usage information can include a smoking liquid level in the container, how many containers have been consumed, and an amount of nicotine consumed. The product information can include a model number and serial number; and the user information can include name, sex, age, address, job, educational background, interests, and hobbies among the information. This data can be stored in memory until downloaded through any suitable wired or wireless connection.

SUMMARY

The exemplary embodiments of the present disclosure provide several advantages over known systems in that the smoking topography device of the present disclosure includes a processor that is configured to look at shifts in battery voltage to determine when smoking events occur. That is, each puff event on an electronic cigarette drains a portion of charge from the battery, which causes a shift in the battery voltage over the duration of the puff event. Thus, the timing, length, and duration of the puff events can be monitored and recorded around these voltage shifts. Data is collected during the smoking events to monitor device operation and user habits. The data is collected and stored in memory in a structured data pattern and can be later transferred to an external device over a USB or wireless connection for further analysis or processing.

The data can be recorded in a hexadecimal format or other suitable format as desired, output through wired or wireless means to an external device and used in clinical studies to monitor smoking topography, and/or to inform smoker of usage. Further, the data can be used to optimize device performance, or calibrate the device based on smoker's usage patterns. For example, the data may be used to optimize device functions such as power modulation, fluid delivery rate, battery voltage, so as to optimize sensory experience and/or extend battery life or heater life.

An exemplary first embodiment is directed to an electronic aerosol smoking article, comprising: at least one sensor configured to measure user interaction with the smoking article; a processor configured to detect a smoking event based an output of the at least one sensor, collect data associated with the smoking event, and arrange the data in a pattern that associates the smoking event to shifts in battery voltage; and memory configured to store the data pattern in a structured multi-byte format.

An exemplary second embodiment is directed to a smoking topography circuit of an electronic aerosol smoking article, the circuit comprising: at least one sensor configured to detect user interaction with the smoking article; a battery configured to supply power to the smoking article; a processor configured to detect a smoking event based on output of the at least one sensor, collect data associated with the smoking event, and arrange the data in a pattern that associates the smoking event to shifts in battery voltage; and memory configured to store the data pattern in a structured multi-byte format.

An exemplary third embodiment of the present disclosure is directed to method of generating smoking topography data for an electronic aerosol smoking article including at least a battery, a heating element, and a processor, the method comprising: determining an occurrence of a smoking event through at least one sensor that measures user interaction with the smoking article; capturing a battery voltage at a start and an end of a smoking event; and generating a data structure that defines the smoking event with respect to a change in battery voltage at the start and end of the smoking event.

BRIEF DESCRIPTION OF THE DRAWINGS

Exemplary embodiments of the present disclosure are described in more detail with reference to the attached drawings.

DETAILED DESCRIPTION

Exemplary embodiments of the present disclosure are directed to an electronic aerosol smoking article having a capability to collect, store, and transmit smoking topography data to an external device such as a computer, workstation, processor, or other suitable device as desired. The smoking article includes on board non-volatile memory (e.g., flash memory) and a processor, such as a programmable logic device, configured to collect smoking topography data such as puff count, puff duration, puff volume and air flow through various integrated sensors. The processor can be configured to transmit the collected data over a wired or wireless interface, such as Bluetooth or a Universal Serial Bus (USB) connection, to the external device.

Figure 1:
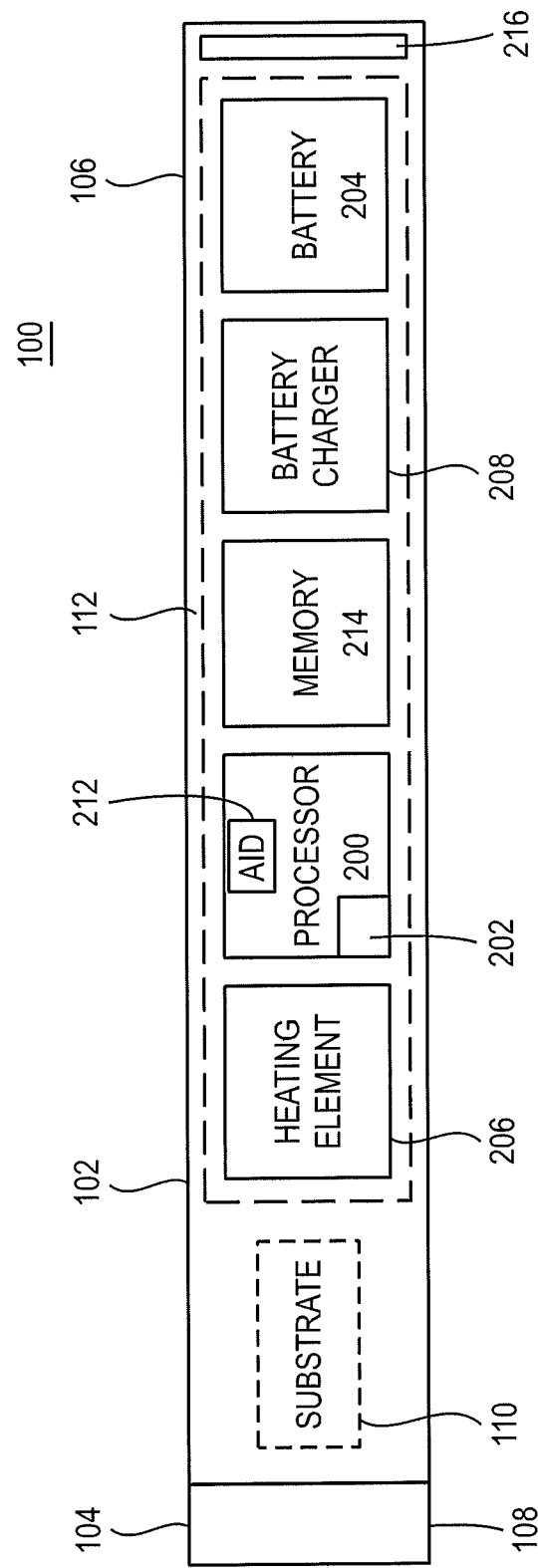
FIG. 1 illustrates an exemplary electronic aerosol smoking article in accordance with an exemplary embodiment of the present disclosure.

FIG. 1 illustrates an exemplary electronic smoking article (e.g., electronic aerosol smoking device (EASD)) 100 in accordance with an exemplary embodiment of the present disclosure. The EASD 100 includes a housing 102 having a first end 104 and a second end 106. The first end 104 includes a mouthpiece 108 configured to be engaged by the mouth of a user. The first end 104 also includes an aerosol forming substrate 110 disposed therein and connected to release aerosol vapors or gas to the user via the mouthpiece 108. The aerosol-forming substrate 110 can include a material comprised of tobacco and volatile tobacco flavored compounds that are released from the substrate upon heating. The aerosol-forming substrate 110 can be implemented in any of a number of known forms. For example, the aerosol-forming substrate 110 can be a solid substrate comprised of any combination of: powder, granules, pellets, shreds, spaghettis, strips or sheets, all of which can include one or more of: herb leaf, tobacco leaf, fragments of tobacco ribs, reconstituted tobacco, homogenized tobacco, extruded tobacco, and expanded tobacco. The solid substrates can be provided on or embedded in any type of suitable thermally stable carrier. In an exemplary embodiment, the aerosol-forming substrate can be a liquid substrate that is retained in any type of known container or porous carrier material. In another exemplary embodiment, the aerosol-forming substrate 110 can be a gas substrate, or any combination of the exemplary aerosol-forming substrates already described.

The second end 106 of the housing 102 can include a smoking topography device 112. The smoking topography device 112 can be connected to the aerosol-forming substrate 110 in the first end 104 of the housing to control the release of aerosol from the aerosol-forming substrate 104 and to collect data associated with the release of the aerosol and use of the EASD 100.

Figure 2:
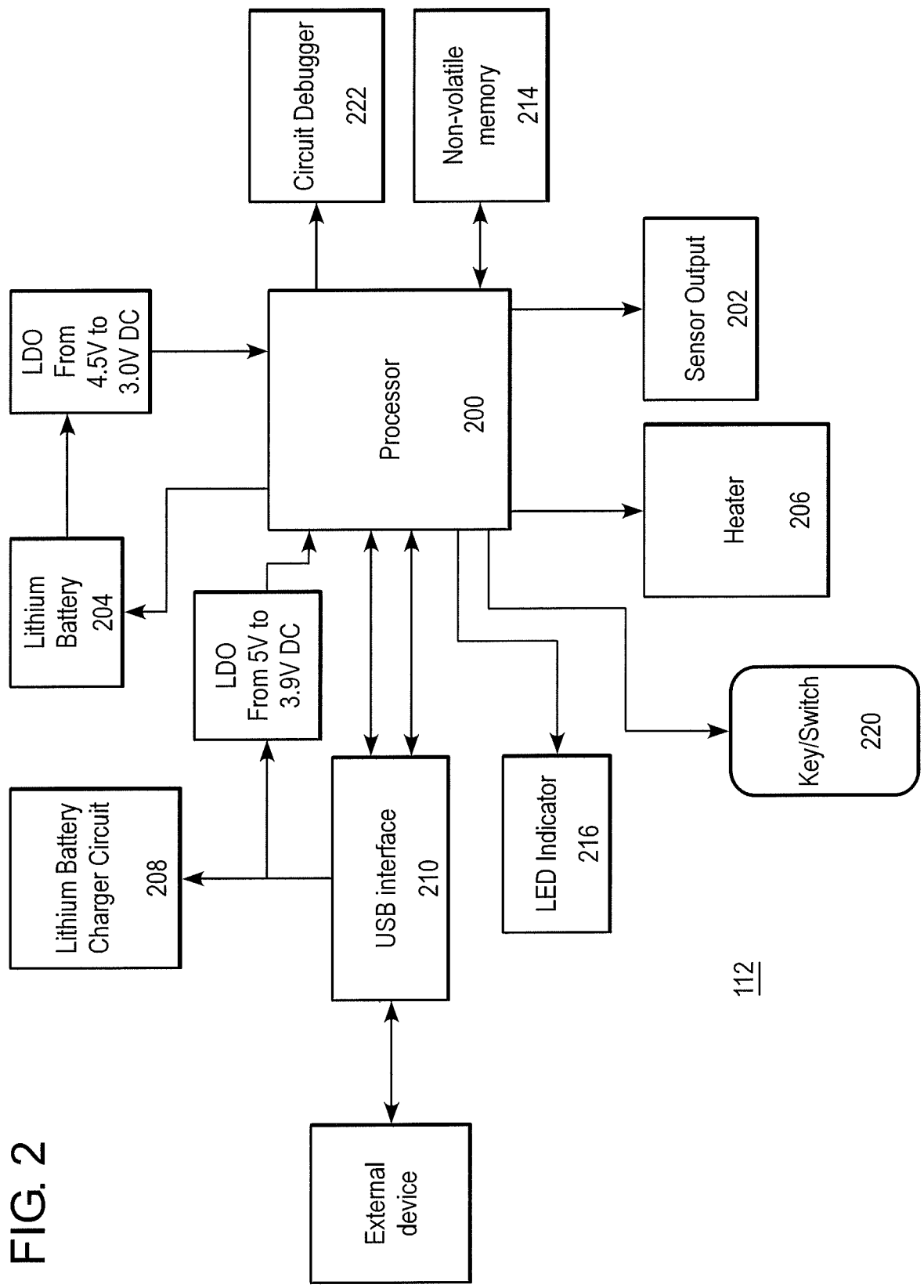
FIG. 2 illustrates features of a smoking topography device (STD) 112 in accordance with an exemplary embodiment of the present disclosure.

FIG. 2 illustrates features of the smoking topography device (STD) 112 in accordance with an exemplary embodiment of the present disclosure.

As shown in FIG. 2, the STD 112 includes a processor 200, a plurality of sensors 202, a power supply 204, a heating element 206, a charging circuit 208, and a communications link 210. The processor 200 can be implemented as a programmable logic circuit, a multi-functional logic chip (MFL), or any other suitable programmable controller or microcontroller device as desired. The processor 200 can be configured to detect a smoking event based on a change in the battery voltage, control the heating element 206 to heat the aerosol-forming substrate 110, and generate a data set based on smoking topography data collected during the smoking event. In an exemplary embodiment, one smoking event can include a puff request event in which the user engages the first end 104 of the housing 102 to effect release of aerosol gas from the mouthpiece 108. Another smoking event can include a puff release event in which the user disengages the first end 104 of the housing 102 thereby stopping the release of aerosol gas from the mouthpiece 108. In another exemplary embodiment, the smoking event can include a combination of a puff request event and a puff release event.

The processor 200 can be configured to include an analog-to-digital (A/D) converter 212 and memory 214. The analog-to-digital (A/D) converter 212 that converts analog data received from any of the plurality of sensors and converts it to digital data. The memory 214, such as a non-volatile Serial Flash memory or other suitable memory device as desired, is configured to store the smoker behavior data converted by the A/D converter 212. The memory can be of sufficient size to store the collected data in multiple data bytes and in a hexadecimal format. The processor 200 is configured to control all operations of the STD 112, such as triggering the heating element 206 to heat the aerosol forming substrate 110, on/off states of the LEDs 216, and other operations to be discussed in further detail below. For example, the processor 200 can be configured to include a system clock (CLK) for tracking the time passed since the initialization of the EASD 100. The processor 200 can also be configured to include various counters (Timer0, Timer1, Timer2, . . . , TimerX) for recording a length, time interval, or duration of a smoking event, a non-smoking time interval between smoking events, or a time after initialization of the EASD 100 and leading up to a smoking event.

The processor 200 can include various other counters (CNT), which can be used to monitor and/or track a number of smoking events (EN) that have occurred. Moreover, the processor can be configured to include any of a number of registers (REG) that can track a status of the system or various components in the system, such as the sensors 202. For example, a battery register (BATTREG) can be configured to record a status of the battery voltage such that a high (1) or low (0) status is recorded based on the voltage level in comparison to a predetermined threshold (e.g., 3.3V). In another example, a smoking status register (SSREG) can be configured to record a status of the EASD 100 during a smoking event as a puff begin status or puff release status. The processor can include a Start of Puff Cigarette Battery Voltage Counts register (SPVCREG) that records a value of the battery voltage level at the instant a puff start event is detected. The processor 200 can also include an End of Puff Cigarette Battery Voltage Count register (EPVCREG) that records a value of the battery voltage level at the instant a puff release event is detected. It should be understood, that any number of registers can be employed to obtain and/or collect data necessary or desired in tracking or monitoring smoking topography.

The plurality of sensors 202 can be configured to measure various functions and operations of the device during a smoking event. The data can include smoking puff length, puff frequency, puff power activity, puff count, air flow rate, or any other smoking topography data related to the smoker as desired. In an exemplary embodiment of the present disclosure, the sensors 200 can be integrated into the structure of the processor 200. In another exemplary embodiment, the at least one of the sensors 200 can be external to the processor.

The power supply 204 can be implemented as a battery or power cell, which supplies power to the heating element 206. The power supply 204 can be in the form of a Lithium-ion battery or any suitable variant thereof. In another exemplary embodiment, the power component 204 can include a Nickel-metal hydride battery or a Nickel cadmium battery or fuel cell. The power supply 204 can be recharged via the charging circuit 208. The charging circuit 208 can be configured to receive power for charging the battery 204 through the communication link 210. Via power converters or other suitable devices, the power supply 204 can be configured to provide power at an appropriate voltage level (e.g., 3.3V) to the processor 200.

The heating element 206 can be configured to include a single element or an array of heating elements. The heating elements 206 can be arranged within the EASD housing 102 so that appropriate heat can be applied to the aerosol-forming substrate. The heating element 206 can include an electrically resistive material such as semiconductor materials including doped ceramics, electrically conductive ceramics, carbon, graphite, metals, metal alloys, composite materials made of ceramic and metallic materials, or any other suitable electrically resistive material as desired. In an exemplary embodiment, the heating element 206 may comprise an electrically resistive coil which cooperates with a filamentary wick, such as described in U.S. published application 2013/0192615. In another exemplary embodiment, the heating element 206 can include an infra-red heating element as described in U.S. Pat. No. 5,514,630 (hereby incorporated by reference in its entirety), an inductive heating element as described in U.S. Pat. No. 5,613,505 (herein incorporated by reference in its entirety), a heat sink or heat reservoir as described in EP 0 857, 431, or any other suitable heating component as desired. The heat reservoir can be comprised of a material capable of absorbing and storing heat and releasing the heat over time to the aerosol-forming substrate. The heat sink or heat reservoir can be in direct contact with the aerosol-forming substrate and can transfer the stored heat directly to the substrate. In other known implementations, the heat stored in the heat sink or heat reservoir can be transferred to the aerosol-forming substrate via a heat conductor, such as a metallic tube, as described in WO 2008/0154441. In any exemplary configuration, the heating element 206 is configured to trigger a heating cycle of the aerosol-forming substrate 110 based on a control signal received from the processor 200.

The communication link 210 can be configured to provide a bi-directional wired or wireless connection to an external device. In a wired configuration, the communication link 210 can be a Universal Serial Bus (USB), a Recommended Standard 232 (RS-232) family of standards. The wired configuration can provide bi-directional communication and also power up to 5V DC. In a wireless configuration, the communication link 210 can be implemented as Bluetooth, Infrared Data Association (IrDA), radio-frequency (RF), cellular, or other suitable wireless communication standard as desired. The communication link 208 is connected to the processor 200 to transfer smoking topography data to the external device and/or the transfer configuration data to the processor 200. The communication link 210 can be configured to allow for bidirectional communication of user data, control data, and/or configuration data between the STD 112 and an external device or processor. With regard to the configuration and control data, the processor 200 can be configured to be specially programmed and/or configured to execute a process recorded on a non-transitory computer-readable recording medium, such as a hard disk drive, flash memory, optical memory or any other type of non-volatile memory as desired. The executable data for the process being transferable or transferred to the processor 200 via the communication link 208.

In an exemplary embodiment, the STD 112 can be configured to include at least one light emitting diode (LED) 218, which provides a visual indication to a user regarding an operational status of the EASD 100. For example, the LEDs can be visualized on an outer portion of the housing 102 and provide a visual indication of a charging status of the battery 202, the smoking status, or any other suitable operational or functional characteristic of the EASD 100 or STD 112 as desired. It should be understood, that the LED can be configured to emit any suitable color, be in any suitable shape, or provide an output in any suitable pattern as desired to provide the appropriate information to the user.

The STD 112 can also include a key/switch circuit 220 that provides secure access to system/configuration data and/or smoking topography data stored in the processor 200.

In another exemplary embodiment the STD 112 can include a circuit debugger 222 that allows for resolving errors in the processing operation of the processor 200 due to corrupted user data, configuration data, or system data as needed.

The STD 112 can be formed on a multi-layer printed circuit board (PCB). The circuit board can be of a suitable size and length, such as 25 mm×8 mm, so that it can be fully enclosed in the housing 102 of the EASD 100.

The STD 112 can be configured to include two modes of operation, which include a Pre-Heat Mode and a Steady Smoking Mode.

When a user starts to smoke (e.g., a smoking event), the heating element is initially cool. Therefore, the heating element 206 can specify to have a full power supplied so that the temperature can be increased as fast as possible. Once the heater is pre-heated, the power supplied to the heating element 206 can be scaled back. In an exemplary embodiment, a pulse-width modulated (PWM) pulse can be provided to the heater to maintain constant power scheme can be used to maintain constant power and temperature in order to extend the life of the heater. Parameters of the PWM pulse can be adjusted through an application interface of a computer via the communication link 210 to select a desired power level for the Steady State Smoking Mode. For example, in an exemplary embodiment in which the pulse width has a large duty cycle, the average output power on the heater would also be larger. The time specified for completing a Pre-Heat Mode depends on the temperature of the heating element just prior to the start of the Pre-Heat Mode. The Pre-Heat time can be adjusted by setting the value of a counter (Timer0), which specifies an idle time between two smoking events.

The communication link 210 can also be used to configure the STD 112, such that different voltage battery levels have different times for completing the Pre-Heat Mode and different PWM pulse values. In an exemplary embodiment, the battery voltage levels can be divided into four ranges as follows: (1) 3.3V-3.5V, (2) 3.5V-3.7V, (3) 3.7V-3.9V, and (4) 3.9V-4.1V. Variable resistors on the PCB board of the STD 112 can be tuned to control the voltage level used by the electronic cigarette device. In an exemplary embodiment of the present disclosure, different pre-heat times can PWM pulse values can be set in the PC interface via the communication link 210 to maintain a desired smoking quality at any of a number of voltage levels. Because the PWM power in one voltage range should be equal to the PWM power in another voltage range, once parameters in a range (1) are determined, for example, the parameters of the other voltage ranges can be derived using the following:

$$P_{PWM(1st\ voltage\ range)} = P_{PWM(2nd\ voltage\ range)} \quad (1)$$

$$P = \frac{V^2}{R} \quad (2)$$

where P is the power of the PWM pulse, V is the average voltage of the PWM pulse, and R is the resistance or value of the period of the PWM pulse.

The duration of the Idle Time is a factor in determining an optimal Pre-Heat time. A longer idle time results in the heater being cooler just prior to starting the Pre-heat Mode, which means that a longer pre-heat time should be specified.

Figure 3:
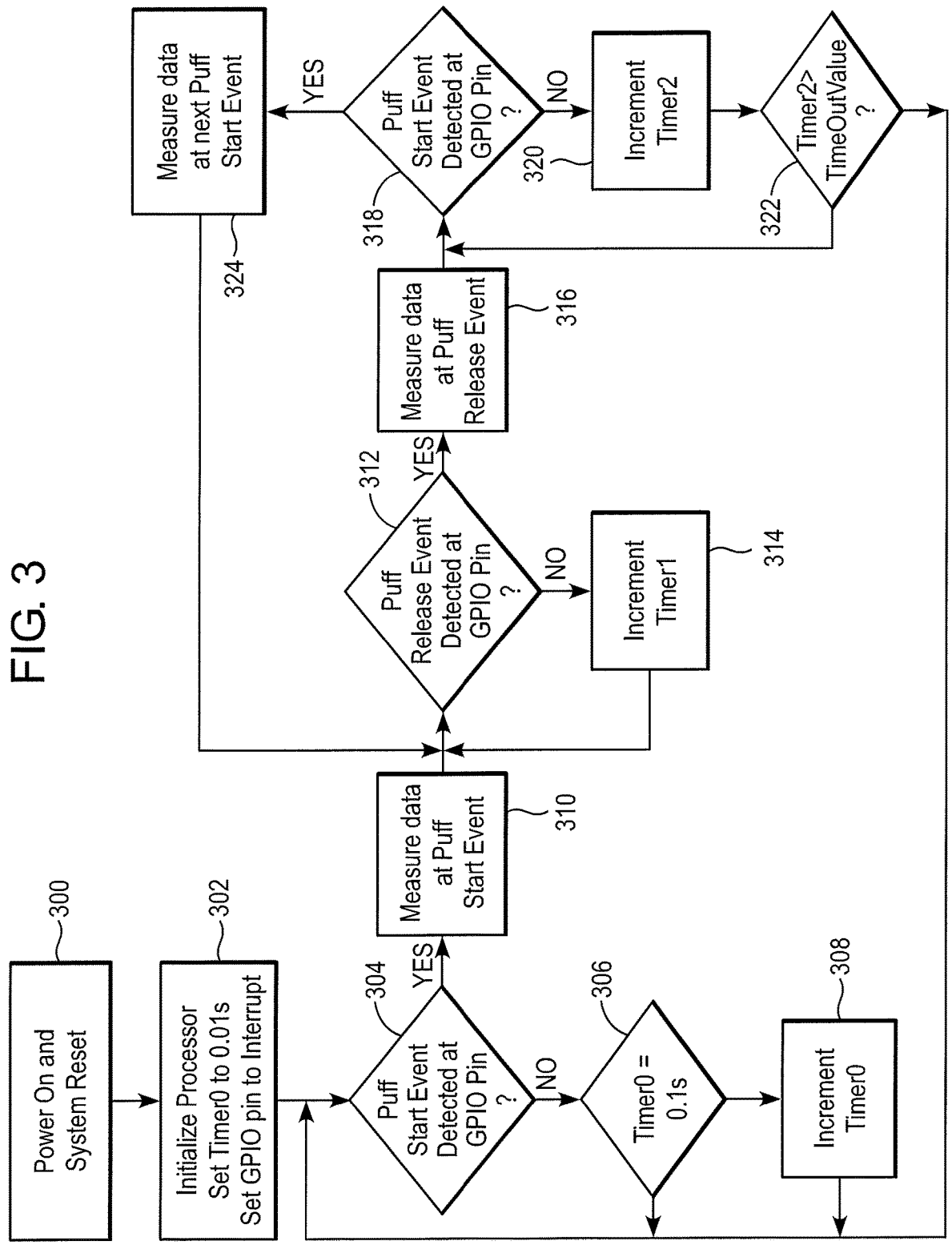
FIG. 3 illustrates a method for generating smoking topography data in accordance with an exemplary embodiment of the present disclosure.

FIG. 3 illustrates a method for generating smoking topography data in accordance with an exemplary embodiment of the present disclosure. As shown in FIG. 3, at step 300, when the STD 112 is powered on or reset, the system program is loaded from memory and initialized. Once the system program and/or configuration data is loaded from memory 214, the processor is provided with at least date information for the system clock.

At step 302, and following system start, the idle time counter (Timer0) and the system clock (CLK) are initialized. Timer0 is set to Pre-Heat Mode idle time set by the user, or is initialized to a default value. The processor also sets at least one general purpose input/output (GPIO) pin as an interrupt (INT) input. For example, in an exemplary embodiment the processor 200 can have a pin (e.g., a Port C1) connected to an output of an air flow sensor. The air flow sensor can be configured to detect a change in the air flow based on a predetermined threshold. This change indicates that a user has engaged or disengaged the mouthpiece 108 of the EASD 100 and initiated or stopped smoking sequence during a puff start event or puff release event, respectively. When the air flow sensor output is connected to a GPIO pin set as an interrupt (Int1), a high or flow sensor output causes the processor to generate interrupt INT1.

At step 304, the processor 200 monitors the GPIO pin. If the GPIO pin is low then the sensor has not detected puff start event or flow. At step 306, when no puff start event is detected, the Timer0 value is 0.1 s, then an interrupt for Timer0 is generated and at step 308, the Timer0 value is incremented. Processing then returns to step 304 and continues to monitor the GPIO pin for a puff start event.

When the air flow sensor output is high indicating a puff start event, then the interrupt INT1 is generated. Once the interrupt INT1 is generated, at step 310 the processor 200 captures a value of the battery voltage and records this value as the Start of Puff Cigarette Battery Voltage Count (SPVC). The processor 200 also initiates a second counter (Timer1), which is used to measure the length of the puff or the time interval from the puff start event to the puff release event. The processor 200 also collects and records a value of the system clock.

At step 312, the processor 200 monitors the GPIO pin connected to the airflow sensor 202. Specifically, the GPIO pin is monitored for a low output, which means that the air flow sensor has detected that the air flow at the mouthpiece 108 has dropped below the predetermined threshold. A low output from the airflow sensor 202 is an indication that a puff release event has occurred. At step 314, when the GPIO pin maintains a high value then the Timer1 is incremented and processing returns to step 312 to again monitor the GPIO pin.

Returning to step 312, when the airflow sensor output is low (0), an interrupt INT2 at the GPIO pin is generated. Upon the generation of INT2, the processor 200 stops the Timer1 and records the value of the Timer1 as the Time of Event (TOE) or puff length (Step 316). The processor 200 then starts a third counter (Timer2), which measures the puff release length or the non-smoking time interval between the puff release event and a puff start event of the next smoking event. The processor 200 collects the value of the battery voltage and records this value as the End of Puff Battery Voltage Count (EPVC). The processor 200 also collects and records a value of the system clock.

Processing continues at step 318, where the GPIO pin is again monitored for a high value indicating another puff start event. If no puff start event is detected, at step 318 the processor 200 increments Timer2 by 1 (step 320). If after incrementing, the value of Timer2 is above a predetermined value then the processor 200 will determine that no further puff events will occur and in order to conserve battery charge will turn off the EASD 100 or go into a sleep mode (step 322). If the value of the Timer2 is otherwise below the threshold value, then processing returns to step 316.

If at step 318, the processor 200 detects a next puff start event, then the value of the Timer2 is collected and recorded, and processing returns to step 312.

Figure 4:
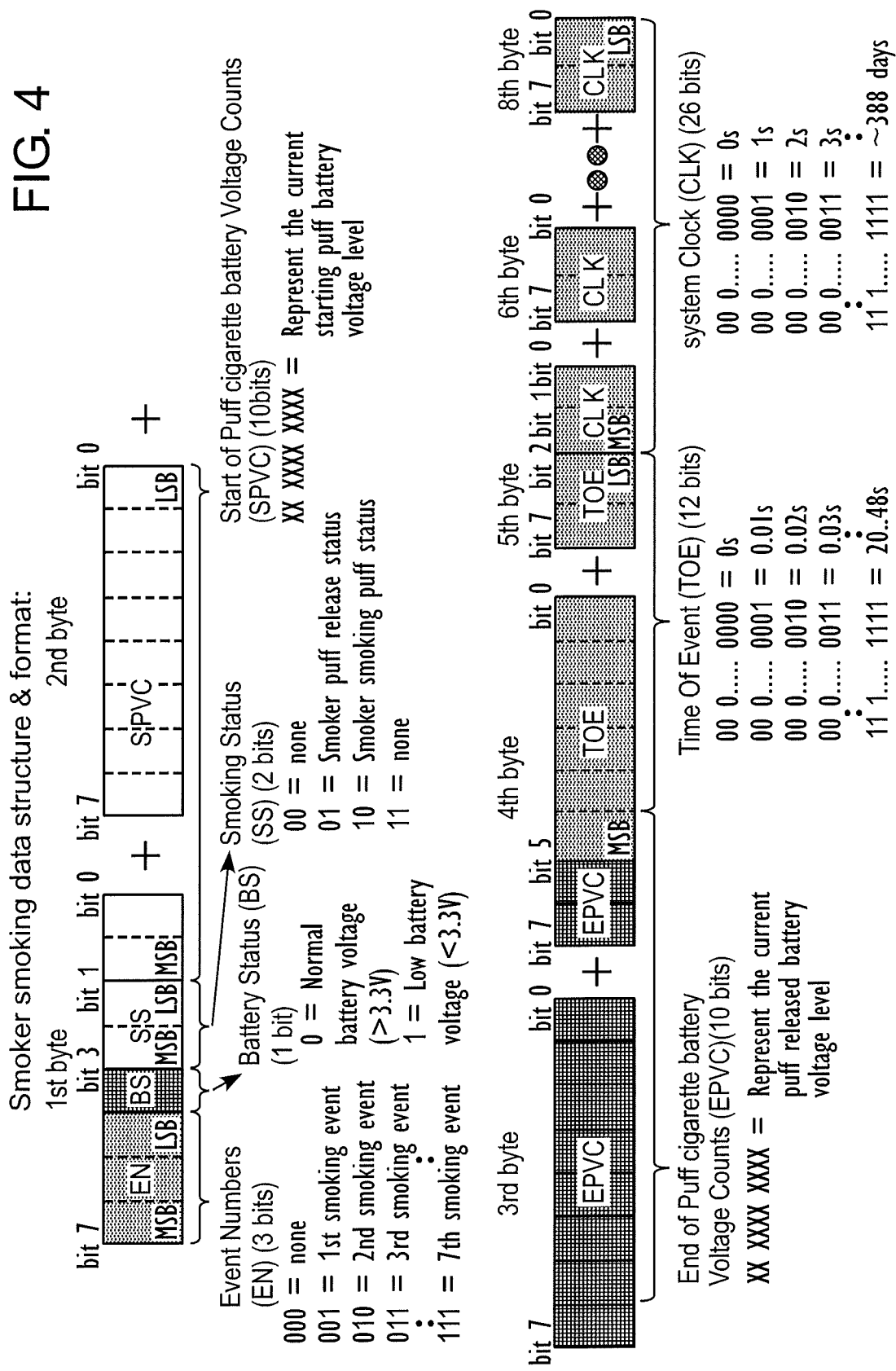
FIG. 4 illustrates a data format and structure in accordance with an exemplary embodiment of the present disclosure.

FIG. 4 illustrates a data format and structure in accordance with an exemplary embodiment of the present disclosure.

As already discussed, the processor 200 collects numerous amounts of data related to the smoking topography through the use of registers and counters, each having a specified bit resolutions. The collected data is transferred to memory 214, where it is recorded in a specified data format and structure. The data is recorded in a corresponding bit pattern such that each byte of data includes a number of bits assigned to at least one specified data value. The multi-byte data structure being stored in a hexadecimal format. As shown in FIG. 4, the data format can include multiple bytes, the first data byte (8 bits) including data values that specify the event number (EN), battery status (BS), and smoking status (SS). The second data byte can include a value corresponding to the SPVC value stoned in the SPVCREG. The third data byte can include EPVC value stored in the EPVCREG. A combination of the fourth and fifth data bytes can be used to record the time of count value as stored in the TOEREG value, and a portion of the fifth data byte along with the sixth through eighth can be used to record a value of the system clock CLKREG. As shown, each data value has a corresponding bit resolution, however, it should be understood that the bit resolution for each data value can be adjusted as desired for suitable monitoring of smoking topography in a specified implementation.

Figure 5:
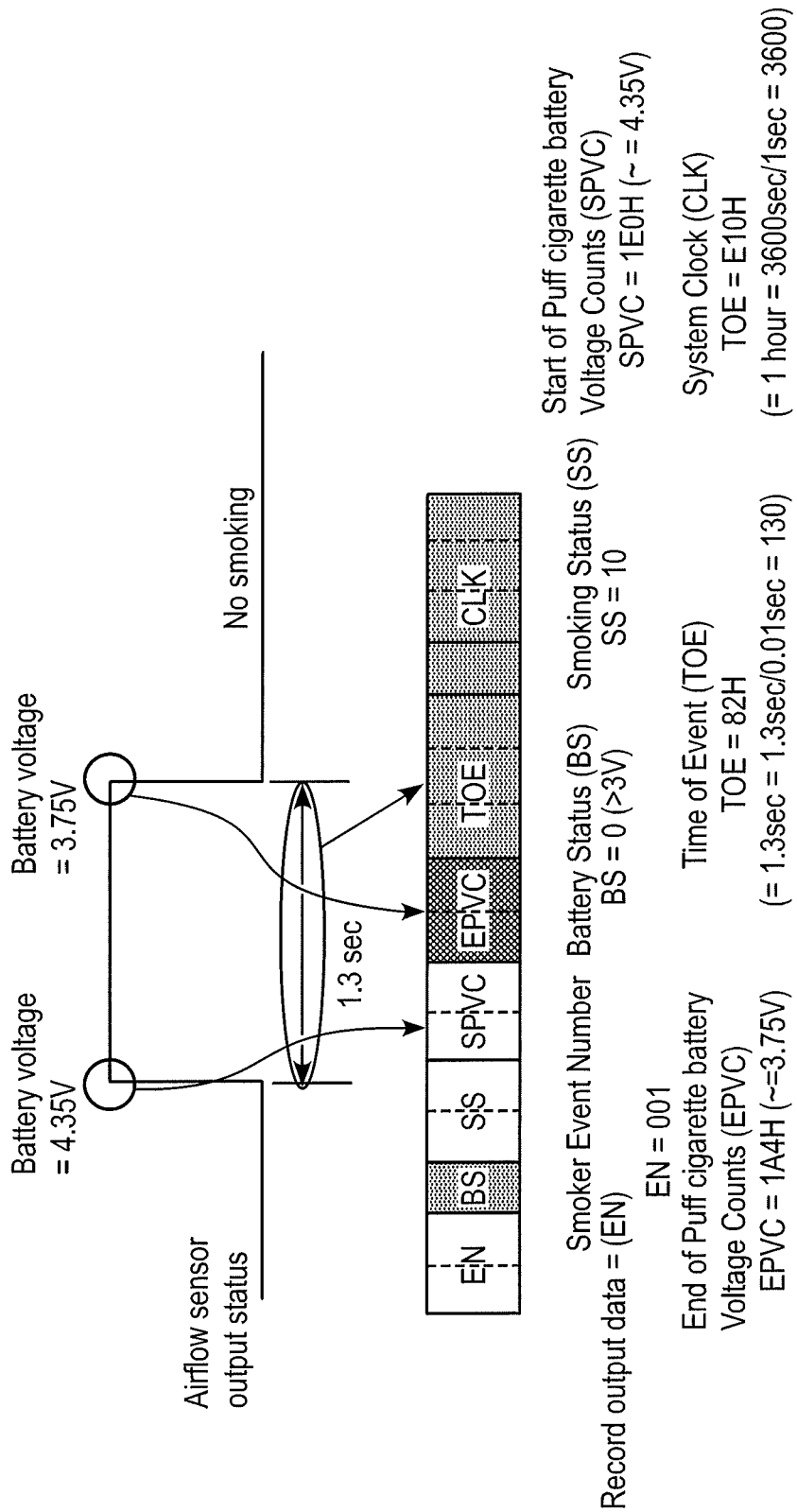
FIG. 5 illustrates an example of smoking topography data as recorded in memory for a single smoking event in accordance with the method as shown in FIG. 3 in accordance with an exemplary embodiment of the present disclosure.

FIG. 5 illustrates an example of smoking topography data as recorded in memory for a single smoking event in accordance with the exemplary method shown in FIG. 3 of the present disclosure. In the context of this example, the single smoking event includes one puff start event and puff release event pair. As shown in FIG. 5, for the single smoking event the processor 200 collected an SPVC value of 4.35V, and EPVC value of 3.75V, a TOE value of 1.3 seconds, and a system clock value of 1 hour. Moreover, the battery status was identified as normal (>3V) and the smoking status identified as a puff status (10). The foregoing data can be recorded in a hexadecimal format and output at a value of 29 E0 6D 02 28 00 0E 10.

Figure 6:
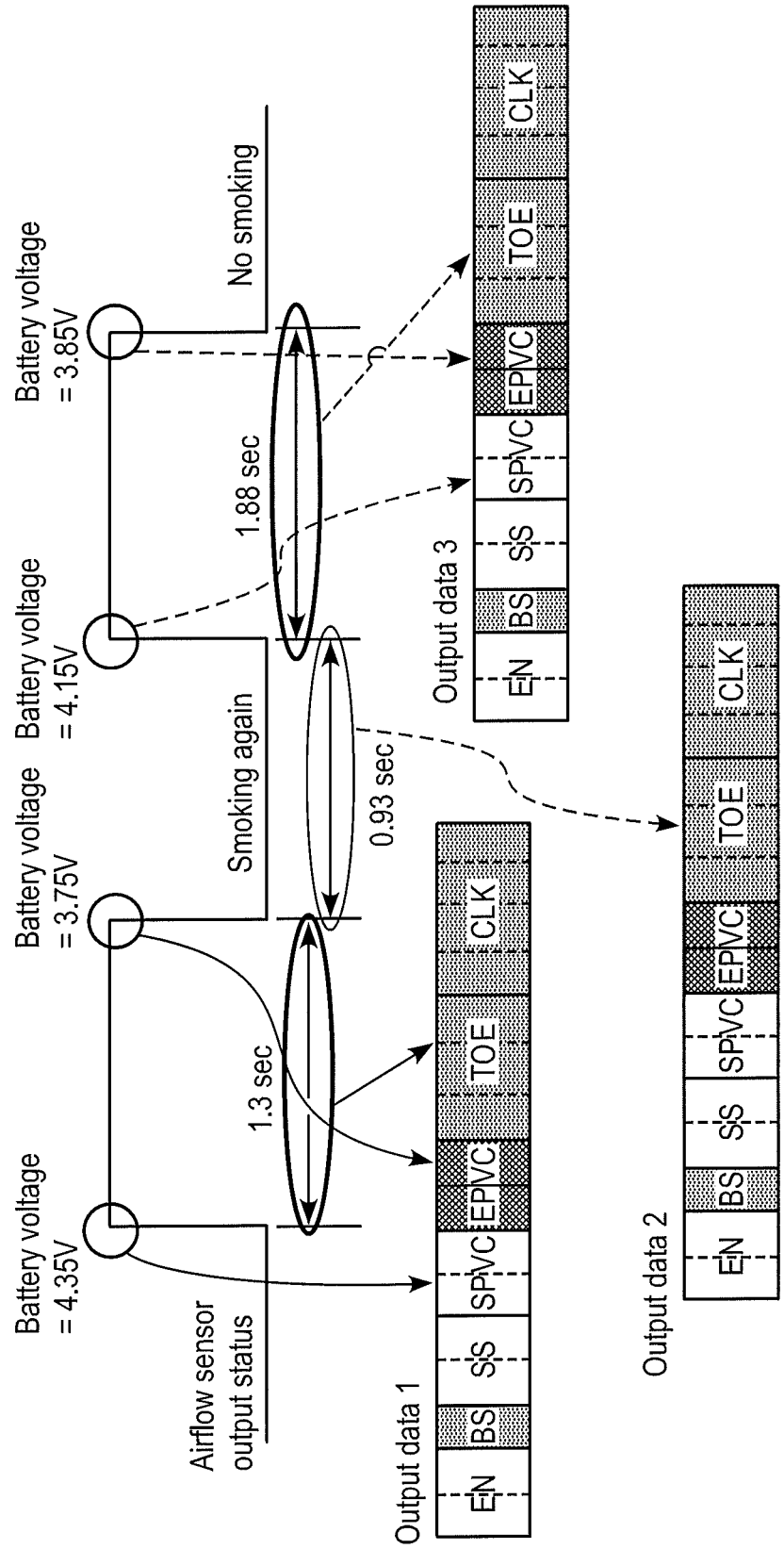
FIG. 6 illustrates an example of smoking topography data recorded in memory for consecutive smoking events in accordance with the method illustrated in FIG. 3 in accordance with an exemplary embodiment of the present disclosure.

FIG. 6 illustrates an example of smoking topography data recorded in memory 214 for consecutive smoking events in accordance with the exemplary method illustrated in FIG. 3 of the present disclosure. In the context of this example, consecutive smoking events include multiple and consecutive puff start and puff release event pairs. As shown in FIG. 6, for the first smoking event the processor 200 collected an SPVC value of 4.35V, and EPVC value of 3.75V, a TOE value of 1.3 seconds, and a system clock value of 1 hour. Moreover, the battery status was identified as normal (>3V) and the smoking status identified as a puff status (10). The data of the first smoking event is recorded in a hexadecimal format and output at a value of 29 E0 6D 02 28 00 0E 10.

For the second smoking event, the processor 200 collected an SPVC value of 0V, and EPVC value of 0V, a TOE value of 0.93 seconds, and a system clock value of 1 hour 1 second. Moreover, the battery status was identified as normal (>3V) and the smoking status identified as a puff release status (01). The data of the second smoking event can be recorded in a hexadecimal format and output at a value of 64 00 00 01 7 40 0E 11. For the third smoking event, the processor 200 collected an SPVC value of 4.15V, and EPVC value of 3.85V, a TOE value of 1.88 seconds, and a system clock value of 1 hour 3 seconds. Moreover, the battery status was identified as normal (>3V) and the smoking status identified as a puff status (10). The data of the third smoking event can be recorded in a hexadecimal format and output at a value of 69 C9 6F 02 F0 00 0E 13.

The teachings herein are applicable to all forms of electronic smoking articles, such as electronic cigarettes, cigars, pipes, hookas, and other smoking articles as desired, regardless of their size and shape.

While the disclosure has been illustrated and described in detail in the drawings and foregoing description, such illustration and description are to be considered illustrative or exemplary and not restrictive; the disclosure is not limited to the disclosed exemplary embodiments. Other variations to the disclosed exemplary embodiments can be understood and effected by those skilled in the art and practicing the claimed disclosure, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference symbols in the claims should not be construed as limiting the scope.

Thus, it will be appreciated by those skilled in the art that the present disclosure can be embodied in other specific forms without departing from the spirit or essential characteristics thereof. The presently disclosed embodiments are therefore considered in all respects to be illustrative and not restricted. The scope of the disclosure is indicated by the appended claims rather than the foregoing description and all changes that come within the meaning and range and equivalence thereof are intended to be embraced therein.

What is claimed is:

1. An electronic vaping article, comprising:
   an aerosol-forming substrate;
   a heating element configured to heat the aerosol-forming substrate to form an aerosol;
   a battery configured to supply power to the heating element to cause the heating element to generate heat;
   an air flow sensor configured to generate an output based on measuring a magnitude of an air flowrate through at least a portion of the electronic vaping article;
   a processor configured to
      detect a start event and an end event of a user interaction with the electronic vaping article based on the output of the air flow sensor and a threshold magnitude value,
      capture battery voltage data indicating a shift in a voltage of the battery associated with the user interaction based on
         capturing a start value of the voltage of the battery in response to detection of the start event,
         capturing an end value of the voltage of the battery in response to detection of the end event, and
         determining the shift in the voltage of the battery associated with the user interaction as a difference between the start value and the end value, and
      arrange the battery voltage data in a data pattern that defines the user interaction with the electronic vaping article by at least the shift in the voltage of the battery such that the start value and the end value are associated with a first interaction event number and an interaction status of the battery in the data pattern, the interaction status of the battery indicating whether the voltage of the battery associated with the user interaction exceeds a threshold battery voltage; and
   a memory configured to store the data pattern in a structured multi-byte format.

2. The electronic vaping article of claim 1, wherein the processor includes a timer configured to be initiated in response to detection of the start event and stopped in response to detection of the end event to obtain a vaping time interval, and the processor is configured to collect a value of the vaping time interval and record the value in the data pattern in association with the first interaction event number as a length of the user interaction with the electronic vaping article.

3. The electronic vaping article of claim 1, wherein
   the electronic vaping article includes a plurality of sensors including the air flow sensor, the plurality of sensors configured to measure the voltage of the battery in response to detection of the start event and detection of the end event.

4. The electronic vaping article of claim 1, wherein
   the first interaction event number is one of a plurality of interaction event numbers recorded in the data pattern and corresponding to a first data set type representing a respective user interaction with the electronic vaping article, for each respective interaction event number among the plurality of interaction event numbers the processor is configured to record in the data pattern in association with the respective interaction event number the interaction status of the battery,
an indication that the respective interaction event number corresponds to the first data set type,
the start value of the voltage of the battery,
the end value of the voltage of the battery,
a time interval of the respective user interaction with the electronic vaping article, and
a value of a system clock included in the electronic vaping article, and
wherein for each respective non-interaction event number among a plurality of non-interaction event numbers recorded in the data pattern and corresponding to a second data set type representing a user non-interaction with the electronic vaping article the processor is configured to record in the data pattern in association with the respective non-interaction event number
a non-interaction status of the battery the non-interaction status of the battery indicating whether a non-interaction voltage of the battery associated with the user non-interaction exceeds the threshold battery voltage,
an indication that the respective non-interaction event number corresponds to the second data set type,
a null start value of the voltage of the battery,
a null end value of the voltage of the battery,
a non-vaping time interval between an end of a first user interaction with the electronic vaping article and a start of a second user interaction with the electronic vaping article, and
the value of the system clock.

5. The electronic vaping article of claim 4, wherein the processor includes a first timer configured to measure a length of each user interaction with the electronic vaping article, and a second timer configured to measure a duration between the first and second user interactions with the electronic vaping article.

6. The electronic vaping article of claim 1, further comprising:
a plurality of sensors including the air flow sensor, the plurality of sensors configured to measure the voltage of the battery, the processor being configured to collect a value of the voltage of the battery from the plurality of sensors, and determine the interaction status of the battery.

7. The electronic vaping article of claim 1, wherein the processor is configured to collect data indicating a start of the user interaction with the electronic vaping article and an end of the user interaction with the electronic vaping article from said air flow sensor and determine a vaping status.

8. The electronic vaping article of claim 7, wherein for the data set generated upon occurrence of the start of the user interaction with the electronic vaping article, the processor is configured to determine that the vaping status is a vaping puff status, and include at least one bit in a data set in the data pattern associated with the first interaction event number indicating the vaping puff status of the electronic vaping article.

9. The electronic vaping article of claim 7, wherein upon an occurrence of consecutive user interactions with the electronic vaping article, for the data set generated upon occurrence of the end of a first user interaction with the electronic vaping article, the processor is configured to determine that the vaping status is a puff release status, and include at least one bit in a data set in the data pattern associated with a first non-interaction event number indicating the puff release status of the electronic vaping article.

10. The electronic vaping article of claim 1, wherein the processor is configured to output a data set associated with the first interaction event number in the data pattern in a hexadecimal format.

11. The electronic vaping article of claim 1, further comprising:
an interface for connecting the processor to an external device.

12. The electronic vaping article of claim 1, wherein the processor includes a system clock, and a value of the system clock is recorded in association with the first interaction event number.

13. A vaping topography circuit of an electronic vaping article, the vaping topography circuit comprising:
an air flow sensor configured to detect user interaction with the electronic vaping article based on measuring a magnitude of an air flowrate through at least a portion of the electronic vaping article;
a heating element configured to heat an aerosol-forming substrate to form an aerosol;
a battery configured to supply power to the heating element to cause the heating element to generate heat;
a processor configured to
detect a start event and an end event of the user interaction with the electronic vaping article based on an output of the air flow sensor and a threshold magnitude value,
capture battery voltage data indicating a shift in a voltage of the battery associated with the user interaction based on
capturing a start value of the voltage of the battery in response to detection of the start event,
capturing an end value of the voltage of the battery in response to detection of the end event, and
determining the shift in the voltage of the battery associated with the user interaction as a difference between the start value and the end value, and
arrange the battery voltage data in a data pattern that defines the user interaction with the electronic vaping article by at least the shift in the voltage of the battery such that the start value and the end value are associated with a first interaction event number and an interaction status of the battery in the data pattern, the interaction status of the battery indicating whether the voltage of the battery associated with the user interaction exceeds a threshold battery voltage; and
a memory configured to record the data pattern in a structured format.

14. The vaping topography circuit of claim 13, wherein the processor includes a timer configured to be initiated in response to detection of the start event and stopped in response to detection of the end event, wherein a value of the timer at the end of the user interaction with the electronic vaping article is recorded in the data pattern in association with the first interaction event number as a length of the user interaction with the electronic vaping article.

15. The vaping topography circuit of claim 13, wherein the first interaction event number is one of a plurality of interaction event numbers recorded in the data pattern and corresponding to a first data set type representing a respective user interaction with the electronic vaping article, for each respective interaction event number among the plurality of interaction event numbers, the processor is configured to record in the data pattern in association with the respective interaction event number representing the respective user interaction with the electronic vaping article at least the start value of the voltage of the battery associated with the respective user interaction, the end value of the voltage of the battery associated with the respective user interaction, the interaction status of the battery, and a length of the respective user interaction with the electronic vaping article, and wherein for each respective non-interaction event number among a plurality of non-interaction event numbers recorded in the data pattern and corresponding to a second data set type representing a user non-interaction with the electronic vaping article the processor is configured to records in the data pattern in association with the respective non-interaction event number at least a duration between consecutive user interactions with the electronic vaping article.

16. The vaping topography circuit of claim 15, wherein the processor includes
a first timer configured to measure the length of the user interaction with the electronic vaping article; and
a second timer configured to measure the duration between the consecutive user interactions with the electronic vaping article.

17. The vaping topography circuit of claim 13, wherein the processor is configured to generate a first interrupt based upon a first output of the air flow sensor corresponding to detection of the start event, and generate a second interrupt upon a second output of the air flow sensor corresponding to detection of the end event, and wherein the processor is configured to determine a vaping status of the electronic vaping article based on the start event and the end event.

18. The vaping topography circuit of claim 17, wherein upon generation of the first interrupt, the processor is configured to determine that the vaping status of the electronic vaping article is a vaping puff status, and records at least one bit in a data set in the data pattern associated with the first interaction event number indicating the vaping puff status.

19. The vaping topography circuit of claim 17, wherein upon generation of the second interrupt, the processor is configured to determine that the vaping status of the electronic vaping article is a puff release status, and records at least one bit in a data set in the data pattern associated with a first non-interaction event number indicating the puff release status.

20. The vaping topography circuit of claim 13, wherein the processor includes
an analog-to-digital converter configured to convert analog data received from the air flow sensor to digital data.

21. A method of generating vaping topography data for an electronic vaping article, the electronic vaping article including at least an aerosol generator including a heating element configured to heat an aerosol-forming substrate to form an aerosol, a battery configured to supply power to the heating element to cause the heating element to generate heat, and an air flow sensor configured to generate an output based on measuring a magnitude of an air flowrate through at least a portion of the electronic vaping article, the method comprising:
determining an occurrence of a start event of a first user interaction with the electronic vaping article based on the output of the air flow sensor and a threshold magnitude value;
capturing first start battery voltage data indicating a voltage of the battery at the start event in response to the determining the occurrence of the start event;
determining an occurrence of an end event of the first user interaction with the electronic vaping article based on the output of the air flow sensor and the threshold magnitude value;
capturing first end battery voltage data indicating a voltage of the battery at the end event in response to the determining the occurrence of the end event;
determining a shift in the voltage of the battery associated with the first user interaction as a difference between the first end battery voltage data and the first start battery voltage data; and
generating a data structure that defines the first user interaction with the electronic vaping article with respect to the shift in the voltage of the battery between the start event and the end event such that the first start battery voltage data and the first end battery voltage data are associated with a first interaction event number and an interaction status of the battery in the data structure, the interaction status of the battery indicating whether the voltage of the battery associated with the first user interaction exceeds a threshold battery voltage.

22. The method of claim 21, wherein the first user interaction with the electronic vaping article includes a puff start event followed by a puff release event.

23. The method of claim 22, further comprising:
generating a first interrupt when the puff start event is detected; and
starting a first timer upon generation of the first interrupt to measure a length of the first user interaction with the electronic vaping article.

24. The method of claim 23, further comprising:
generating a second interrupt when the puff release event is detected;
stopping the first timer upon generation of the second interrupt; and
starting a second timer upon generation of the second interrupt to measure a duration until a next puff start event.

25. The method of claim 24, further comprising:
storing the captured first start battery voltage data and first end battery voltage data, the interaction status of the battery, and values for the first and second timers, in association with the first interaction event number in a structured format in a non-volatile memory.

26. The method of claim 21, at power on or reset, comprising:
loading system programming stored in memory to a processor; and
initializing the system programming in the processor.

27. The method of claim 26, the method further comprising:
starting a first timer when the system programming is initialized in the processor for a pre-heat mode; and
setting, in the processor, at least one sensor port as an interrupt.

28. The method of claim 21, wherein first interaction event number is one of a plurality of interaction event numbers included in the data structure, the data structure including at least second start battery voltage data and second end battery voltage data in association with a second interaction event number corresponding to a second user interactions with the electronic vaping article, and the data structure includes a duration between user interactions with the electronic vaping article as an event length in association with a non-interaction event number.

29. The method of claim 21, further comprising:
optimizing at least one function of the electronic vaping article based on data included in the data structure.

30. The method of claim 29, wherein the optimizing includes configuring at least one of,
a pulse-width modulation (PWM) pulse provided to the heating element, and
a duration during which the heating element receives full power in a pre-heat mode.

* * * * *